United States Patent [19]

Gee et al.

[11] 4,122,029
[45] Oct. 24, 1978

[54] EMULSION COMPOSITIONS COMPRISING A SILOXANE-OXYALKYLENE COPOLYMER AND AN ORGANIC SURFACTANT

[75] Inventors: Ronald P. Gee; Joseph W. Keil, both of Midland, Mich.

[73] Assignee: Dow Corning Corporation, Midland, Mich.

[21] Appl. No.: 819,210

[22] Filed: Jul. 27, 1977

[51] Int. Cl.$^2$ ............................................. B01J 13/00
[52] U.S. Cl. ................................... 252/309; 252/321; 252/358; 252/308
[58] Field of Search ............... 252/309, 321, 358, 308; 424/170

[56] References Cited

U.S. PATENT DOCUMENTS

| | | | |
|---|---|---|---|
| 3,234,252 | 2/1966 | Pater | 252/49.6 X |
| 3,489,690 | 1/1970 | Lachampt et al. | 252/309 X |
| 3,562,786 | 2/1971 | Bailey et al. | 252/526 X |

FOREIGN PATENT DOCUMENTS 742,289  9/1966  Canada.

OTHER PUBLICATIONS

The Condensed Chemical Dictionary (8th Ed.), revised by Gessner G. Hawley (1974), pp. 346, 937.

Primary Examiner—Benjamin R. Padgett
Assistant Examiner—E. Suzanne Parr
Attorney, Agent, or Firm—George A. Grindahl

[57] ABSTRACT

Stable emulsions of a polar liquid in a non-polar base liquid are prepared with the cooperating action of a mixture of a water-in-oil surfactant having an HLB value of from 2 to 10 and certain polydiorganosiloxane-polyoxyalkylene copolymers. An emulsion of interest is an anti-perspirant composition comprising an aqueous solution of aluminum chlorhydrate as the polar liquid dispersed in cyclopolydimethylsiloxanes as the non-polar base liquid, using a mixture of nonylphenoxy polyethoxyethanol and a copolymer of a trimethylsiloxane-endblocked polydimethylsiloxane containing a minor amount of methylhydrogensiloxane units and an allyloxy-endblocked polyoxyethylenepolyoxypropylene copolymer.

6 Claims, No Drawings

EMULSION COMPOSITIONS COMPRISING A SILOXANE-OXYALKYLENE COPOLYMER AND AN ORGANIC SURFACTANT

BACKGROUND OF THE INVENTION

This invention relates to emulsions of a polar liquid in a non-polar liquid. In one aspect this invention relates to aqueous solutions-in-polydimethylsiloxane emulsions using a mixture of a silicon-free emulsifier and a silicon-containing copolymer as the emulsifying agent. In another aspect this invention relates to aqueous emulsions which are dilutable with paraffinic hydrocarbons.

Water-in-oil emulsions are well known and there exists many organic emulsifiers which are operable for their preparation and stabilization. For example, Lachampt, et al., U.S. Pat. No. 3,489,690 describes water-in-oil emulsions using certain polyoxyalkylene alcohols as the emulsifiers. The oil phase may comprise silicone oils which are soluble in the oil. When one attempts to prepare a water-in-low-viscosity polydimethylsiloxane emulsion, however, said organic emulsifiers do not provide suitably stable emulsions. This is especially noticeable when the aqueous phase contains a dissolved solute.

Aqueous lubricating compositions are taught by Pater, U.S. Pat. No. 3,234,252 which employ a siloxane-polyoxyalkylene copolymer as an additive. These compositions are said to be either solutions or water-in-oil emulsions or oil-in-water emulsions; however, no water-in-oil emulsions are indicated. Moreover, Pater's concentrated compositions are described as being dilutable with water or mixtures of water and an organic lubricant base fluid, thereby suggesting that said emulsions are oil-in-water emulsions. When one attempts to prepare water-in-low viscosity polydimethylsiloxane emulsions, using only a siloxane-polyoxyalkylene copolymer as an emulsifier, suitably stable emulsions are not obtained, although they are frequently more stable than when prepared using only organic surfactants.

We have found that stable emulsions of a polar liquid, e.g. water, in a non-polar liquid, e.g. a polydimethylsiloxane fluid can be prepared if a mixture of certain organic surfactants and certain polydiorganosiloxane-polyoxyalkylene copolymers is used as the emulsifying agent.

Mixtures of organic surfactants and siloxane-oxyalkylene copolymers have been used before. For example, a siloxane-oxyalkylene block copolymer has been used by Bailey, et al. U.S. Pat. No. 3,562,786 to lower the surface tension of an aqueous solution of an organic surfactant, however, these compositions are oil-in-water emulsions.

Water-in-oil siloxane emulsions are disclosed by Nitzsche, et al., Canadian Patent No. 742,289; however, the oil in these compositions is a siloxane-polyoxyalkylene copolymer and does not comprise a non-polar liquid such as a polydimethylsiloxane or a paraffinic hydrocarbon.

SUMMARY OF THE INVENTION

It is an object of this invention to provide stable emulsions of polar liquids in non-polar liquids.

It is another object of this invention to provide stable emulsions of polar liquids in low-viscosity polydimethylsiloxanes.

It is another object of this invention to provide stable emulsions of aqueous solutions in low-viscosity polydimethylsiloxanes.

It is another object of this invention to provide stable emulsions of aqueous solutions in low-viscosity polydimethylsiloxanes which are dilutable with paraffinic hydrocarbons.

These and other objects are realized by the compositions of this invention wherein a polar liquid is dispersed in a non-polar base liquid by the cooperating action of a mixture consisting essentially of certain organic water-in-oil surfactants and certain polydiorganosiloxane-polyoxyalkylene copolymers.

The polar liquid, which is insoluble in the non-polar base liquid, is the dispersed phase and the base liquid is the continuous phase in the compositions of this invention.

Compositions of this invention wherein the polar liquid comprises water, such as aqueous solutions of personal care products such as insect repellants and anti-perspirants and the base liquid comprises a polydimethylsiloxane, such as cyclopolydimethylsiloxanes are of particular interest because of the aesthetic value of the feel of said composition when applied to the human skin.

Compositions of this invention are also of particular interest because they are dilutable with gaseous paraffinic hydrocarbons and are thus adaptable as a spraycan formulation.

DESCRIPTION OF THE INVENTION

This invention relates to an emulsion composition consisting essentially of (a) 1 to 70 percent by weight of a polar liquid as a dispersed phase, (b) 17 to 97.5 percent by weight of a non-polar base liquid as a continuous phase, said base liquid having a viscosity at 25° C. of up to 100 millipascal-seconds and being selected from the group consisting of methylsiloxane fluids of the average unit formula $(CH_3)_a SiO_{(4-a)/2}$ wherein $a$ has an average value of from approximately 2 to 3 inclusive and paraffinic hydrocarbon fluids, (c) 0.5 to 3 percent by weight of an organic water-in-oil surfactant having an HLB value of from 2 to 10, and (d) 1 to 10 percent by weight of a polydiorganosiloxane-polyoxyalkylene copolymer containing at least one polydiorganosiloxane segment consisting essentially of $R_b SiO_{(4-b)/2}$ siloxane units wherein $b$ has a value of from 0 to 3, inclusive, there being an average of approximately 2 R groups per silicon for all siloxane units in the copolymer, and R denotes a radical selected from the group consisting of methyl, ethyl, vinyl, phenyl, and a divalent radical bonding a polyoxyalkylene segment to the polydiorganosiloxane segment, at least 95 percent of all R being methyl; and at least one polyoxyalkylene segment having an average molecular weight of at least 1,000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from 2 to 8 and the total of (a) plus (b) plus (c) plus (d) being 100 percent by weight.

Polar liquid (a) of the compositions of this invention is the dispersed phase therein and may comprise one or more effacacious components such as an anti-perspirant, a humectant, an insect repellent, an odorant, a deodorant, an emollient, an antiseptic, a sunscreen agent, a cleansing agent, and a suitable pharmaceutical.

The polar liquid (a) may be any suitable liquid composition which is insoluble at room temperature in the base oil, hereinafter described. By polar it is meant a substance which has a permanent dipole moment. Of course, to maintain the identity of the compositions of this invention the polar liquid should not undergo chemical reaction with remaining components of the composition. The polar liquid may be a pure liquid or a liquid solution or a mixture of immiscible liquids, the components of which are polar and insoluble in the base liquid. Solid polar materials may be used as component (a) if they are changed to a liquid form such as by heating to melt the solid or by dissolving the solid in a solvent.

Exemplary of suitable materials which are polar include inorganic materials such as water, salts, weak acids, weak bases and aqueous solutions thereof and organic materials bearing polar groups such as organic compounds bearing nitrogen-containing groups such as in amides, amines, amine salts, nitriles, imides, imines, lactams, and nitro compounds; oxygen-containing groups such as in ethers, alcohols, and in carbonyl groups such as in ketones, aldehydes, carboxylic acids and their salts, esters and lactones; phosphorus-containing groups such as in phosphates and phosphonium salts; sulfur-containing groups such as in sulfones, mercaptans, sulfoxides and sulfides; and halogens such as in hydrocarbon chlorides, bromides, and iodides. The presence of said polar groups in the organic material provides a permanent dipole moment and thus provides the polar character in the organic material.

Emulsion compositions of this invention wherein the polar liquid comprises water and/or ethanol are particularly useful. In common with oil-in-water emulsions, water-in-oil emulsions are desirable from an economic, safety and environmental viewpoint as a means of preparing, storing, shipping, and using effacacious components. In addition, emulsion compositions of aqueous or ethanolic solutions in methylsiloxane fluids have value as personal care compositions, as noted above.

Polar liquids (a) of particular interest for the compositions of this invention are therefore selected from the group consisting of water, water solutions of polar solutes, polar liquids soluble in water, ethanol, ethanol solutions of polar solutes and polar liquids soluble in ethanol. Suitable water solutions comprise, as the polar solute, inorganic solutes hereinbefore exemplified and organic solutes such as alcohols such as methanol, ethanol, phenol, ethylene glycol, propylene glycol, glycerine, and their partial ethers and partial esters; nitrogen compounds such as amides such as formamide, acetamide, N-methylacetamide, N,N-dimethyl formamide and urea, nitriles such as acetonitrile and amines and their salts, acids such as formic acid, acetic acid, benzoic acid, stearic acid, and ethylenediaminetetracetic acid and ethers such as furan, tetrahydrofuran, dioxane, ethylene glycol dimethyl ether, propylene glycol dimethylether and their polymeric forms such as triethylene glycol diethyl ether. Suitable ethanol solutions comprise as the solute, any suitable water-soluble inorganic or organic solute exemplified above as well as other polar solutes which are insoluble in water but soluble in ethanol such as 2-ethyl-1,3-hexanediol, N,N-diethyltoluamide and 2-ethylhexyl-p-dimethylaminobenzoate.

The non-polar base liquid (b) of the compositions of this invention has a viscosity of up to 100 millipascal-seconds at 25° C. and is a methylsiloxane fluid, a paraffinic hydrocarbon or their mixtures.

The methylsiloxane fluid corresponds to the average unit formula $(CH_3)_aSiO_{(4-a)/2}$ where $a$ has an average value of from 2 to 3. The methylsiloxane fluid comprises siloxane units joined by Si-O-Si bonds selected from the group consisting of $(CH_3)_3SiO_{1/2}$, $(CH_3)_2SiO_{2/2}$, $CH_3SiO_{3/2}$ and $SiO_{4/2}$ units taken in such molar amounts so that there is an average of from approximately two to three methyl groups per silicon in the methylsiloxane fluid and said fluid has a viscosity of no more than 100 millipascal-seconds at 25° C.

Preferably the methylsiloxane fluid (b) consists essentially of dimethylsiloxane units, and optionally, trimethylsiloxane units. Of particular value as a base liquid in volatile compositions, such as cosmetic lotions, are methylsiloxane fluids having a viscosity of less than 10 millipascal-seconds such as the cyclopolysiloxanes of the general formula $\{(CH_3)_2SiO\}_x$ and linear siloxanes of the general formula $(CH_3)_3SiO\{(CH_3)_2SiO\}_ySi(CH_3)_3$ wherein $x$ is an integer of from 3 to 8 and $y$ is an integer of from 0 to 4.

Paraffinic hydrocarbon fluids suitable for use in these compositions correspond to the average unit formula $C_nH_{2n+2}$, in the well-known manner, wherein $n$ is an integer having a value such that the paraffinic hydrocarbon is fluid at room temperature. Of particular vaue as a base liquid in volatile compositions are the paraffins having a value of $n$ less than 15 such as kerosene, gasoline, and the gaseous paraffins. Of course, gaseous paraffins, in order to be operative in the dispersions of this invention, must be used at low temperature and/or super-atmospheric pressure to keep them in the liquid state.

The base oil, in addition to being a methylsiloxane fluid or a paraffin, may be any mixture of said methylsiloxane fluid and said paraffin such as a mixture of octamethylcyclotetrasiloxane and hexane or decamethylcyclopentasiloxane and butane or a mixture of two or more of said cyclosiloxanes and one or more paraffins.

It has been discovered that the emulsion compositions of this invention are stable to dilution with a paraffinic hydrocarbon. This is of particular advantage in the preparation of emulsions of aqueous solutions of polar materials in a methylsiloxane fluid which will not break when formulated as a spray-can composition being a gaseous paraffin such as isobutane as the propellant.

Methylsiloxane fluids and paraffinic hydrocarbons suitable for use as non-polar base fluid (b) in the compositions of this invention are well known in the chemical and polymer arts; many are commercially available.

Component (c) is any organic surfactant suitable for preparing emulsions of the water-in-oil type and having an HLB (hydrophilic-lipophilic balance) value of from 2 to 10 inclusive. Said surfactant may be anionic, cationic or non-ionic with respect to its hydrophilic portion. Examples of suitable surfactants include sodium capryl lactylate and sodium stearoyl lactylate as anionic surfactants, quaternary ammonium chlorides manufactured by Tomah Products, Inc. as Emulsifier Three™ and Emulsifier Four™ as a cationic surfactant and polyethylene glycol (200) monolaurate, glycerol monolaurate, N,N-dimethylcaproamide, diethylene glycol monolaurate, sorbitan monolaurate and nonylphenoxy polyethoxyethanol as non-ionic surfactants. Other examples of suitable organic surfactants having an HLB value of from 2 to 10 may be found by reference to standard publications such as McCutcheon's, *Detergents and Emulsifiers*, Allured Publishing Company, Ridgewood, NJ 1974.

Component (d) is a polydiorganosiloxanepolyoxyalkylene block copolymer containing at least one polydiorganosiloxane block and at least one polyoxyalkylene block. The polyoxyalkylene blocks may be bonded to the polydiorganosiloxane blocks with silicon-oxygen-carbon bonds and/or with silicon-carbon bonds. For compositions of this invention wherein the polar liquid (a) comprises water it is preferred that the block copolymer have silicon-carbon bonding instead of the more hydrolyzable silicon-oxygen-carbon bonding joining the polyoxyalkylene blocks to the polydiorganosiloxane blocks.

The polydiorganosiloxane blocks of the block copolymer (d) consist essentially of siloxane units which are interlinked by Si-O-Si linkages and which have the formula $R_bSiO_{(4-b)/2}$. The value of $b$ may range from 0 to 3 for said siloxane units with the provision that there is an average of approximately 2, i.e. from 1.9 to 2.1 R groups for every silicon in the block copolymer. Suitable siloxane units thus include $R_3SiO_{1/2}$, $R_2SiO_{2/2}$, $RSiO_{3/2}$, and $SiO_{4/2}$ siloxane units taken in such molar amounts so that $b$ has an average value of approximately 2 in the block copolymer. Said siloxane units may be arranged in linear, cyclic and/or branched fashion.

The R radicals of colymer (d) may be any radical selected from the group consisting of methyl, ethyl, vinyl, phenyl, and a divalent radical bonding a polyoxyalkylene block to the polydiorganosiloxane block. At least 95 percent of all R radicals in the block copolymer (d) are methyl radicals, preferably there is at least one methyl radical bonded to each silicon atom in (d).

Divalent R radicals bonding a polyoxyalkylene block to a polydiorganosiloxane block may be bonded to the siloxane units of said polydiorganosiloxane block by a silicon-oxygen bond or by a silicon-carbon bond. As noted above, silicon-carbon bonding between polydiorganosiloxane blocks and polyoxyalkylene blocks is preferred in those compositions of this invention comprising water. Divalent R radicals preferably contain no more than 6 carbon atoms. Illustrative of divalent R radicals include —O—, —$C_mH_{2m}O$—, —$C_mH_{2m}$— and —$C_mH_{2m}CO_2$— where $m$ is an integer.

Illustrative of the siloxane units that make up the polydiorganosiloxane blocks of the block copolymer (d) are as follows, where Me denotes methyl and Q denotes said divalent R radical bonding a polyoxyalkylene block: $R_3SiO_{1/2}$ units such as $Me_3SiO_{1/2}$, $Me_2(CH_2=CH)SiO_{1/2}$, $Me_2(C_6H_5)SiO_{1/2}$, $Me(C_6H_5)(CH_2=CH)SiO_{1/2}$, $Me_2(CH_3CH_2)SiO_{1/2}$, $Me_2QSiO_{1/2}$, $MeQ_2SiO_{1/2}$, $Q_3SiO_{1/2}$, $Q_2(CH_3CH_2)SiO_{1/2}$, and $Me(C_6H_5)(Q)SiO_{1/2}$; $R_2SiO_{2/2}$ units such as $Me_2SiO_{2/2}$, $Me(C_6H_5)SiO_{2/2}$, $Me(CH_2=CH)SiO_{2/2}$, $(C_6H_5)_2SiO_{2/2}$, $MeQSiO_{2/2}$, and $Q(C_6H_5)SiO_{2/2}$; $RSiO_{3/2}$ units such as $MeSiO_{3/2}$, $C_6H_5SiO_{3/2}$, $CH_2=CHSiO_{3/2}$, $CH_3CH_2SiO_{3/2}$ and $QSiO_{3/2}$; and $SiO_{4/2}$ units.

It is to be understood that block copolymer (d) may comprise one or more of said polydiorganosiloxane blocks, multiple polydiorganosiloxane blocks being linked by polyoxyalkylene blocks. The number of and average molecular weight of the polydiorganosiloxane blocks in the copolymer is related to the desired weight ratio, hereinafter described, of said blocks in the copolymer. Preferably block copolymer (d) comprises one polydiorganosiloxane block having bonded thereto one or more polyoxyalkylene blocks.

The polyoxyalkylene blocks of the block copolymer (d) consist essentially of oxyethylene units of the formula —$CH_2CH_2O$—, alone, or in combination with oxypropylene units of the formula —$CH_2CH(CH_3)O$—, an average of at least half of the oxyalkylene units in the polyoxyalkylene blocks being oxyethylene units. Suitable emulsions of this invention are not formed when the polyoxyalkylene blocks contain more than 50 mol percent of the comparatively hydrophobic oxypropylene unit. The polyoxyalkylene blocks thus correspond to the formula $\{-CH_2CH_2O-\}_p\{-CH_2CH(CH_3)O-\}_q$ wherein the oxyalkylene units may be arranged in any suitable fashion such as random, alternating and block. The average values of $p$ and $q$ are such that $p \geq q$ and the sum of $p + q$ is sufficient to provide an average molecular weight of at least 1,000 for the polyoxyalkylene blocks. Preferably the average molecular weight of the polyoxyalkylene blocks has a value of from 1,500 to 5,000.

The polyoxyalkylene blocks of the block copolymer (d) are bonded to the polydiorganosiloxane blocks of said copolymer by at least one terminal portion of said polyoxyalkylene block, said bonding being by way of a divalent R radical, hereinbefore described. It is to be understood that said bonding may be by both terminal portions of said polyoxyalkylene block in those block copolymers comprising more than one polydiorganosiloxane block. Any terminal portion of the polyoxyalkylene block of block copolymer (d) that is not bonded to a polydiorganosiloxane block is satisfied by a terminating radical. The type of said terminating radical is not critical and may be monovalent, thereby terminating one polyoxyalkylene block, or polyvalent, thereby terminating more than one polyoxyalkylene block. Said terminating radicals are made up of atoms selected from the group consisting of carbon, hydrogen, nitrogen, and oxygen. Illustrative of said terminating radical are hydrogen; hydroxyl; alkyl, such as methyl, ethyl, propyl, butyl; benzyl; aryl, such as phenyl; alkoxy such as methoxy, ethoxy, propoxy, butoxy; glyceroxy; benzyloxy; aryloxy, such as phenoxy; alkenyloxy, such as vinyloxy and allyloxy; acyloxy, such as acetoxy, acryloxy and propionoxy and amino such as dimethylamino.

The number of and average molecular weights of the blocks in the block copolymer (d) are such that the weight ratio of polydiorganosiloxane blocks to polyoxyalkylene blocks in block copolymer (d) has a value of from 2 to 8. This weight ratio will insure that the block copolymer (d) has a preferential solubility in the non-polar base liquid, a condition necessary for the formation of stable water-in-oil type emulsions of this invention. Although it is not critical it has been found that there is a direct relationship between the viscosity of the non-polar base liquid and the optimum value for said weight ratio. Base liquids of lower viscosity respond optimally to block copolymers having the lower values for said weight ratio. For example, a preferred emulsion of this invention wherein the non-polar base liquid has a viscosity of less than 10 millipascal-seconds at 25° C. is optimally prepared when the weight ratio of polydiorganosiloxane blocks to polyoxyalkylene blocks has a value of from 2.5 to 4.0.

The weight ratio of polydiorganosiloxane blocks to polyoxyalkylene blocks in block copolymer (d) is calculated on the basis of the total weight of polydiorganosiloxane and the total weight of polyoxyalkylene that is joined in the copolymerization process. For example, if 100 parts by weight of polydiorganosiloxane is joined completely by an addition process, hereinafter described, with 20 parts by weight of polyoxyalkylene, said weight ratio of the resulting copolymer has a value of 5. Of course, if said complete joining is accomplished by a displacement reaction, resulting in the formation of a by-product as hereinafter described, the weight ratio of polydiorganosiloxane to polyoxyalkylene in the resulting block copolymer may not be identical with the weight ratio of the corresponding reactants, due to the loss of the weight of the displaced groups. The error introduced into the calculation of said weight ratio by ignoring the loss of said displaced groups is usually insignificant. That is to say, the weight ratio of polydiorganosiloxane to polyoxyalkylene in copolymer (d) may be calculated from the weight of reactants that react to form the copolymer or said weight ratio may be calculated by suitable analysis of the resulting copolymer itself. Suitable analytical techniques such as elemental analysis, nuclear magnetic resonance spectroscopy, silicon substituent analysis and infra-red spectroscopy may be found in "Analysis of Silicones," A. Lee Smith, Ed., John Wiley and Sons, New York, 1974.

The polydiorganosiloxane-polyoxyalkylene block copolymers (d) useful in the emulsion compositions of this invention may be prepared by any method suitable for block copolymer formation. Herein, block copolymer means either an end-to-end arrangement of blocks such as denoted by the formulae $(AB)_c$, $A(BA)_c$ and $B(AB)_c$ or a pendant arrangement of blocks such as $(AB_d)_c$ or combinations thereof wherein A denotes a polydiorganosiloxane block, B denotes a polyoxyalkylene block and $c$ and $d$ denote integers greater than zero and greater than one, respectively. Typically, block copolymer (d) is prepared by reacting preformed polydiorganosiloxanes and polyoxyalkylenes each bearing suitably coreactive groups. For example, in one method leading to silicon-carbon bonding between blocks a polydiorganosiloxane, free of vinyl radicals and bearing a suitable number of silicon-bonded hydrogen atoms, is reacted in an addition reaction with a polyoxyalkylene bearing a site of terminal aliphatic unsaturation such as allyloxy. This type of reaction is well known and may be illustrated generally as follows:

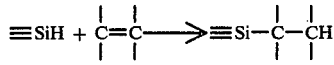

In another suitable method for preparing a block copolymer (d) containing silicon-carbon bonding between blocks a polydiorganosiloxane bearing silicon-bonded haloalkyl groups such as —CH$_2$Cl, —CH$_2$CH$_2$Cl or —CH$_2$CH$_2$CH$_2$Cl is reacted in a displacement reaction, preferably under the influence of a hydrogen halide scavenger, with a polyoxyalkylene bearing an active hydrogen such as —OH. This displacement reaction is well known in the organic chemistry art and may be illustrated generally as follows:

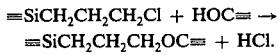

In addition, block copolymer (d) may, if desired, be prepared by the interaction of a polydiorganosiloxane with a polyoxyalkylene which leads to silicon-oxygen-carbon bonding between blocks. For example, a polydiorganosiloxane segment bearing silicon-bonded hydrolyzable radicals may be reacted with a hydroxyl-bearing polyoxyalkylene. Suitable silicon-bonded hydrolyzable radicals include hydrogen, hydroxy, alkoxy, such as methoxy, ethoxy, and isopropoxy; halo, such as fluoro, chloro, bromo, and iodo; amido, such as N-methylacetamido; oximo such as methylethylketoximo; aminoxy, such as diethylaminoxy and acyloxy, such as acetoxy and propionoxy. These hydrolyzable radicals and their reactions are well known in the organosilicon art and may be illustrated generally as follows wherein Z denotes the hydrolyzable radical.

While the polydiorganosiloxane-polyoxyalkylene block copolymers which are suitable for use in the compositions of this invention are new, analogous copolymers are known in the art. Block copolymers (d) may be prepared by modifications of the well-known methods described in the polydiorganosiloxanepolyoxyalkylene copolymer art. The aforementioned patents to Pater and Bailey and the following patents are hereby incorporated by reference to show the preparation of polydiorganosiloxanepolyoxyalkylene block copolymers: Haluska, U.S. Pat. No. 2,868,824; Haluska, Re 25,727; Bailey, U.S. Pat. No. 3,172,899; Simmler, et al. U.S. Pat. No. 3,174,987; Bailey, et al., U.S. Pat. Nos. 3,600,418 and 3,629,308 and Holdstock, U.S. Pat. No. 3,629,165.

It is to be understood that the silicon-bonded reaction groups such as silicon-bonded hydrogen for addition reactions or silicon-bonded hydrolyzable radicals for displacement reactions are preferably completely reacted in the copolymer preparation process, but that trace amounts of said reaction groups may escape reaction with the polyoxyalkylene and may be found in the copolymer (d).

The amounts of polar component (a) and base liquid (b) that may be emulsified may vary widely and comprise, in total, from 87 to 98.5 percent by weight of the composition containing components (a) through (d). Polar component (a) may comprise from 1 to 70, preferably 1 to 50, weight percent of the composition and base oil (b) may comprise from 17 to 97.5 weight percent of the composition. The compositions of this invention may comprise from 0.5 to 3 weight percent of the water-in-oil surfactant and from 1 to 10 weight percent of the polydimethylsiloxane-polyoxyalkylene copolymer, based on the total weight of components (a) through (d). In general, small amounts of polar component may be emulsified in large amounts of base oil with the use of small amounts of the water-in-oil surfactant and the block copolymer.

Small amounts of non-essential components, well known to the emulsion art, and particularly to the cosmetic art, may be added. Exemplary of said non-essential components are colorants, viscosity control additives, and the like.

The compositions of this invention may be prepared by mixing the individual components in any suitable manner in the desired proportions. Preferably the polar component (a) is mixed with a mixture of the base liquid (b), the surface-active agent (c) and the copolymer (d). If the polar component is a solid it is converted to a liquid form by melting or dissolving before the emulsion is formed, as hereinbefore noted. Mixing may be done using standard emulsion techniques.

The compositions of this invention are especially useful as volatile cosmetic compositions wherein the polar component or the base oil evaporates after the composition is applied to a substrate, such as the human skin.

Now in order that those skilled in the art may better understand how the present invention can be practiced, the following examples are given by way of illustration and not by way of limitation. All percentages and parts are by weight, all viscosities were measured in centipoise at 25° C. and were converted to pascal-seconds by multiplying by 0.001 and all pressures were measured in millimeters of mercury and were converted to pascals by multiplying by 133.3224 and rounding off.

EXAMPLE 1

A polydiorganosiloxane-polyoxyalkylene block copolymer was prepared from a trimethylsiloxane-endblocked polydimethylsiloxane having a molecular weight of approximately 30,000 and having an average of approximately 4 of its dimethylsiloxane units replaced with methylhydrogensiloxane units, and a random equimolar polyglycol copolymer of ethylene oxide and propylene oxide having an average molecular weight of approximately 2550 and having allyloxy endgroups on one end and acetoxy endgroups on the other end. Two hundred twenty grams of the siloxane, 80.76 grams of the polyglycol and 75.19 grams of isopropanol were mixed and heated to reflux under dry nitrogen in a flask and the resulting solution was catalyzed with 0.15 ml. of a 1 molar solution of $H_2PtCl_6$ in isopropanol. The reaction mixture was heated at reflux for one hour and then devolatilized at 110° C. and 1.33 kilopascals pressure. The polydimethylsiloxanepolyoxyalkylene copolymer product had a siloxane/oxyalkylene weight ratio of approximately 2.7 and $-CH_2CH_2CH_2O-$ divalent radicals bonding the polyoxyalkylene blocks to the polydimethylsiloxane block by way of a silicon-carbon bond.

EXAMPLE 2

A composition of this invention was prepared by blending on a colloid mill 5 parts of the block copolymer of Example 1, 50 parts of a 50 percent solution of aluminum chlorohydrate in water, 1.5 parts of a polyoxyethylene alkylaryl ether having an HLB value of 8.6 (Hodag ® Nonionic E-4) and 43.5 parts of a mixture of octamethylcyclotetrasiloxane and decamethylcyclopentasiloxane having a viscosity of less than 10 millipascal-seconds at 25° C. The resulting mixture was then passed through a homogenizer to give an emulsion which did not separate at room temperature in six months. An analogous composition was also prepared with a polydimethylsiloxane-polyoxyalkylene polymer similar to that of Example 1 except the weight ratio of siloxane to polyoxyalkylene had a value of 2.1 instead of 2.7.

EXAMPLE 3

A polydimethylsiloxane-polyoxyalkylene copolymer having a weight ratio of 2.2 was prepared as in Example 1, except that an average of approximately 5.4 of the dimethylsiloxane units in the siloxane portion were replaced with methylhydrogensiloxane units. A composition of this invention was prepared by mixing on an Eppenbach high-shear mixer 5 parts of the above copolymer, 1.5 parts of sorbitan monolaurate (Span ® 20), 43.5 parts of a mixture of cyclopolydimethylsiloxanes having a viscosity of less than 10 millipascal-seconds and 50 parts of distilled water as the polar component. The resulting emulsion was stable for at least 6 months at room temperature.

EXAMPLE 4

A polydimethylsiloxane-polyoxyalkylene copolymer having a siloxane to polyoxyalkylene ratio of 3.3 was prepared as in Example 1 except that the siloxane had approximately 3.5 of its dimethylsiloxane units replaced by methylhydrogen siloxane units. An emulsion was prepared by mixing on an Eppenbach mixer two parts of the above copolymer, 2 parts of sorbitan monolaurate, 50 parts of cyclopolydimethylsiloxanes, 32 parts of water and 14 parts of N,N-diethyltoluamide, The resulting emulsion experienced creaming within 4 months at room temperature but did not break.

EXAMPLE 5

A polydimethylsiloxane-polyoxyalkylene copolymer having a siloxane to oxyalkylene weight ratio of 2.8 was prepared as in Example 1. Ten parts of this block copolymer was dissolved in 90 parts of a paraffinic hydrocarbon liquid solid as Isopar ® M by Exxon Corporation. An emulsion composition of this invention was prepared by mixing 50 parts of a 50 weight percent solution of aluminum chlorohydrate in water as the polar liquid, 1.5 parts of Hodag ® Nonionic E-4 as the organic water-in-oil surfactant and 48.5 parts of the above Isopar ® M solution. The emulsion thus had 43.7 parts of Isopar ® M as the non-polar base liquid and 4.8 parts of the polydimethylsiloxane-polyoxyalkylene copolymer.

EXAMPLE 6

A polydiorganosiloxane having an average of approximately 7.5 silicon bonded hydrogens per molecule was prepared by heating a mixture of 6.51 parts of polymethylhydrogen siloxane, 2.44 parts of hexamethyldisiloxane, 491.1 parts of cyclopolydimethylsiloxane and 0.15 parts of trifluoromethane sulfonic acid. After heating for 5 hours at 65° C. The mixture was cooled, the acid was neutralized with $NaHCO_3$; and the neutralized fluid was filtered. One hundred parts of the filtered polydiorganosiloxane was copolymerized with 47.1 parts of a polyoxyalkylene containing 80 mol percent ethylene oxide and 20 mol percent propylene oxide and having an average molecular weight of 1700. The polyoxalkylene was terminated on one end by an allyloxy radical and on the other end by a acetoxy radical. The resulting block copolymer had a siloxane to polyoxyalkylene weight ratio of 2.1.

An emulsion composition of this invention was prepared as in Example 2 except that an Eppenbach high shear mixer was used instead of a homogenizer and the 5 parts of the block copolymer of Example 1 was replaced with 5 parts of the block copolymer of this example. The resulting emulsion was non-flowable and had an average particle size of less than 0.5 μm.

That which is claimed is:

1. An emulsion composition consisting essentially of
   (a) 1 to 70 percent by weight of a polar liquid as a dispersed phase,
   (b) 17 to 97.5 percent by weight of a non-polar base liquid as a continuous phase, said base liquid having a viscosity at 25° C. of up to 100 millipascal-seconds and being selected from the group consisting of methylsiloxane fluids having the average unit formula $(CH_3)_a SiO_{(4-a)2}$ wherein $a$ has an average value of from approximately 2 to 3 inclusive and mixtures thereof with paraffinic hydrocarbon fluids, (c) 0.5 to 3 percent by weight of an organic water-in-oil surfactant having an HLB value of from 2 to 10 inclusive, and (d) 1 to 10 percent by weight of a polydiorganosiloxanepolyoxyalkylene copolymer containing at least one polydiorganosiloxane segment consisting essentially of $R_b SiO_{(4-b)2}$ siloxane units wherein $b$ has a value of from 0 to 3, inclusive, there being an average value of approximately 2 R groups per silicon for all siloxane units in the copolymer, and R denotes a radical selected from the group consisting of methyl, ethyl, vinyl, phenyl, and a divalent radical bonding a polyoxyalkylene segment to the polydiorganosiloxane segment, at least 95 percent of all R being methyl; and at least one polyoxyalkylene segment having an average molecular weight of at least 1000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from 2 to 8 and the total of (a) plus (b) plus (c) plus (d) being 100 percent by weight.

2. The emulsion composition according to claim 1 wherein the polar liquid (a) is an aqueous solution of a polar solute.

3. The emulsion composition according to claim 2 wherein the polyoxyalkylene segments of the polydiorganosiloxane-polyoxyalkylene copolymer (d) are bonded to the polydiorganosiloxane segments by silicon-carbon bonds.

4. The emulsion composition according to claim 3 wherein the non-polar base liquid (b) comprises a siloxane fluid having a viscosity of less than 10 millipascal-seconds at 25° C.

5. The emulsion composition according to claim 4 wherein the weight ratio of polydiorganosiloxane segments to polyoxyalkylene segments in the polydiorganosiloxane-polyoxyalkylene copolymer (d) has a value of from 2.5 to 4.0.

6. The emulsion composition according to claim 5 wherein the copolymer (d) contains one polydiorganosiloxane segment.

* * * * *

UNITED STATES PATENT AND TRADEMARK OFFICE
CERTIFICATE OF CORRECTION

PATENT NO. : 4,122,029
DATED : October 24, 1978
INVENTOR(S) : Ronald P. Gee; Joseph W. Keil It is certified that error appears in the above—identified patent and that said Letters Patent are hereby corrected as shown below:

In Column 10, line 44; the word reading "The" should read "the".

In Column 11, line 3; the formula reading "$(CH_3)_a SiO_{(4-a)2}$" should read "$(CH_3)_a SiO_{(4-a)/2}$".

In Column 11, line 13; the formula reading "$R_b SiO_{(4-b)2}$" should read "$R_b SiO_{(4-b)/2}$".

Signed and Sealed this

Twenty-second Day of September 1981

[SEAL]

Attest:

Attesting Officer

GERALD J. MOSSINGHOFF

Commissioner of Patents and Trademarks